United States Patent [19]

Sakata et al.

[11] Patent Number: 5,296,378
[45] Date of Patent: Mar. 22, 1994

[54] METHOD FOR CLASSIFYING LEUKOCYTES BY FLOW CYTOMETRY

[75] Inventors: Takashi Sakata; Tomoyuki Kuroda, both of Kakogawa, Japan

[73] Assignee: Toa Medical Electronics Co., Ltd., Kobe, Japan

[21] Appl. No.: 947,784

[22] Filed: Sep. 18, 1992

Related U.S. Application Data

[63] Continuation of Ser. No. 663,090, Feb. 28, 1991, Pat. No. 5,175,109, which is a continuation of Ser. No. 91,663, Sep. 1, 1987, abandoned.

[30] Foreign Application Priority Data

Sep. 10, 1986 [JP] Japan .................... 61-213716
Nov. 27, 1986 [JP] Japan .................... 61-282697

[51] Int. Cl.$^5$ .................................. G01N 33/49
[52] U.S. Cl. .................... 436/63; 436/172; 250/459.1; 356/39; 356/336
[58] Field of Search .......... 436/8, 17, 18, 63, 166, 436/172, 175, 176, 179, 800; 424/3, 7.1; 356/39, 335, 336; 250/459.1, 461.2

[56] References Cited

U.S. PATENT DOCUMENTS

| | | | |
|---|---|---|---|
| 3,684,377 | 8/1972 | Adams et al. | 356/36 |
| 3,883,247 | 5/1975 | Adams | 356/39 |
| 3,916,197 | 10/1975 | Fulwyler | 250/361 |
| 3,916,205 | 10/1975 | Kleinerman | 250/461 |
| 4,066,395 | 1/1978 | Soiron et al. | 8/169 |
| 4,073,739 | 2/1978 | Peters | 252/62.1 P |
| 4,252,534 | 2/1981 | Abel et al. | 8/617 |
| 4,400,370 | 8/1983 | Kass | 424/3 |
| 4,528,256 | 7/1985 | Lind | 430/83 |
| 4,581,223 | 4/1986 | Kass | 424/3 |
| 4,666,812 | 5/1987 | Wiedemann et al. | 430/78 |
| 4,751,179 | 6/1988 | Ledis et al. | 435/34 |
| 4,751,188 | 6/1988 | Valet | 436/63 |
| 4,760,006 | 7/1988 | Pawlowski | 430/78 |
| 4,882,284 | 11/1989 | Kirchanski et al. | 436/63 |
| 4,933,293 | 6/1990 | Kuroda et al. | 436/63 |

FOREIGN PATENT DOCUMENTS

0086951A1 8/1983 European Pat. Off. .

OTHER PUBLICATIONS

Shapiro et al., "Combined Blood Cell Counting and Classification with Fluorochrome Stains and Flow Instrumentation," The Journal of Histochemistry and Cytochemistry, 24(1), 396–411 (1976).
Kamentsky, L. A., "Objective Measures of Information From Blood Cells," Blood Cells, 6, 17–36 (1980).
Groner, W. and Tycko, D., "Characterizing Blood Cells by Biophysical Measurements in Flow," Blood Cells 6, 141–157 (1980).
Steinkamp, J. A., "Flow cytometry," Rev. Sci. Instrum. 55(9) 1375–1400 (Sep. 1984).
Shapiro, H. M., "Fluorescent Dyes for Differential Counts by Flow Cytometry: Does Histochemistry Tell Us Much More Than Cell Geometry?," The Journal of Histochemistry and Cytochemistry, 25(8), 976–989 (1977).
*Colour Index*, 3rd Ed., vol. 4, published by The Society of Dyers and Colourists, 4417–4459 (1971).
*Encyclopaedia of Microscopic Stains*, by Edward Gurr, The Williams and Wiklins Co., Baltimore, 319 (1960).
*Encyclopaedia of Microscopic Stains*, by Edward Gurr, The Williams and Wilkins Co., Baltimore, pp. 13–16, 46, 144, 148, 155–156, 173, 201, 290–292, 341, 345–346, 348 (1960).

*Primary Examiner*—James C. Housel
*Assistant Examiner*—Jeffrey R. Snay
*Attorney, Agent, or Firm*—Fitch, Even, Tabin & Flannery

[57] ABSTRACT

A method for classifying leukocytes with a flow cytometer by use of optical measurements on fluorochrome-stained blood cells. The method comprises the steps of lysing erythrocytes in a blood sample, selectively staining eosinophils and basophils, permitting stained sample to flow through a flow cytometer, and identifying and counting the type of each leukocyte.

1 Claim, 9 Drawing Sheets

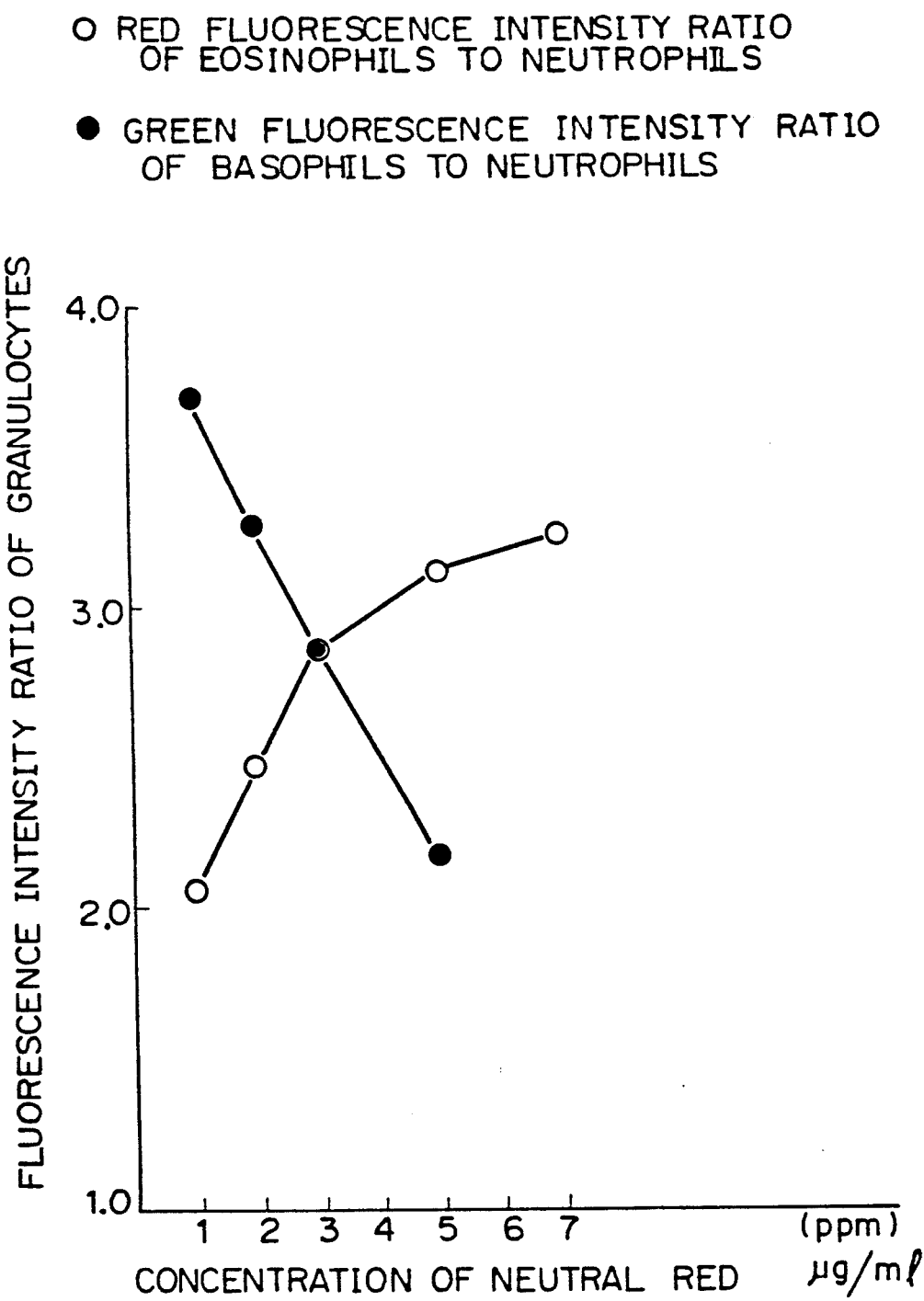

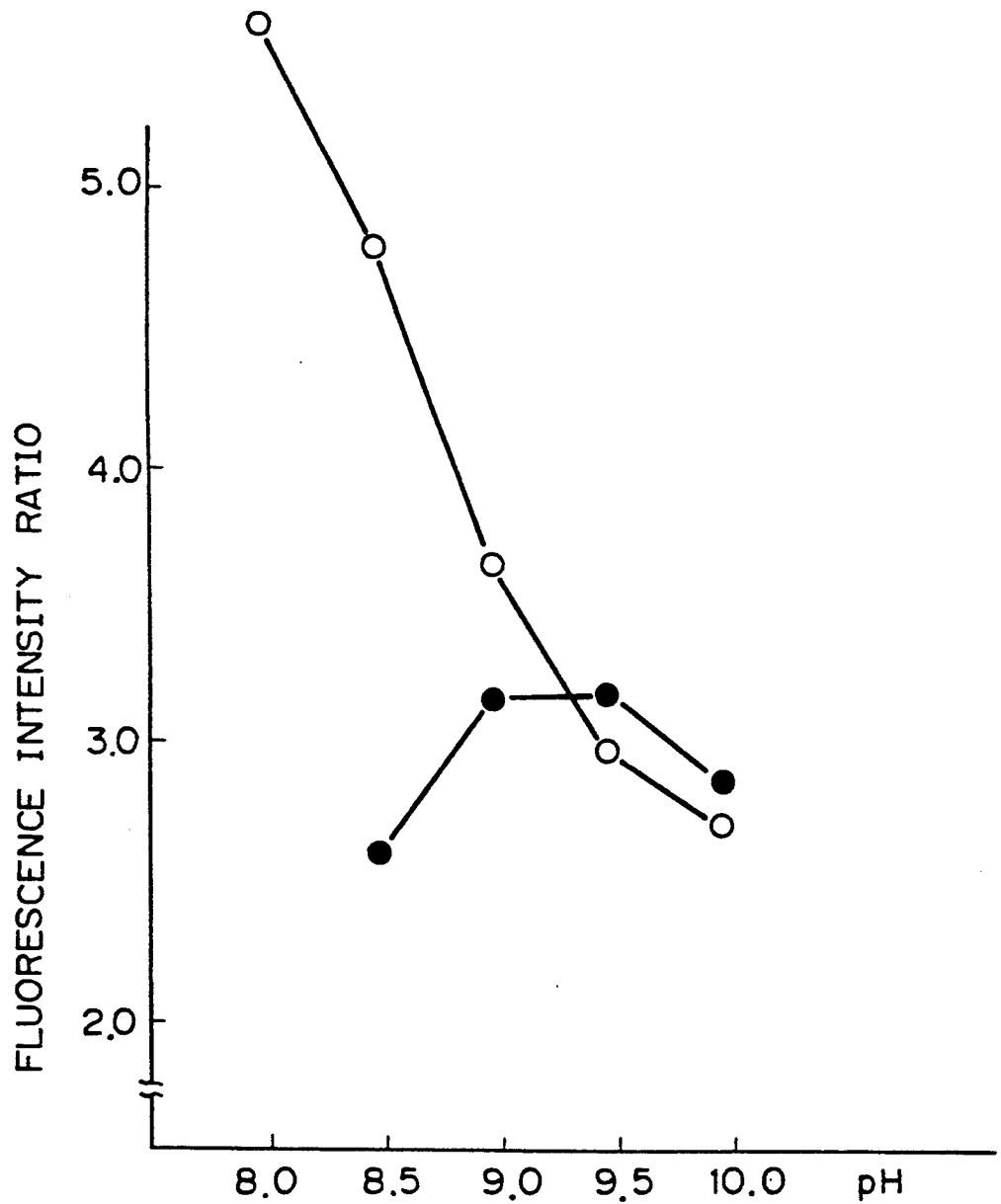

METHOD FOR CLASSIFYING LEUKOCYTES BY FLOW CYTOMETRY

This is a continuation of application Ser. No. 07/663,090, filed Feb. 28, 1991, now U.S. Pat. No. 5,175,109 which was a file wrapper continuation of application Ser. No. 07/091,663, filed Sep. 1, 1987, abandoned.

The present invention relates to a reagent and a method for classifying leukocytes in the practice of clinical testing. More particularly, the present invention relates to a reagent and a method for classifying leukocytes with a flow cytometer by means of optical measurements on fluorochrome-stained blood cells.

Leukocytes in the peripheral blood of normal subjects can be classified as being of five types consisting of lymphocytes, monocytes, neutrophils, eosinophils, and basophils. Different leukocyte types have different functions and counting of leukocytes in the blood according to their type will provide valuable information for diagnostic purposes. For instance, an increase in the number of neutrophils, is associated with such diseases as inflammations, myocardial infarction and leukemia, and a decrease in their number is associated with viral diseases, hypoplastic anemia, agranulocytosis, etc. On the other hand, an increase in the number of eosinophils is found in such diseases as parasitosis, Hodgkin's disease and allergosis. An increased number of monocytes occurs either during the convalescence period of patients suffering from infectious diseases or in such diseases as monocytic leukemia.

Classification and counting of leukocytes have been made most commonly by the differential counting method which is also referred to as the visual counting method or simply as the manual method. In this method a blood sample is spread on a glass slide and the blood corpuscles in the smear are fixed and stained for examination by microscopy. The technician identifies the type of individual leukocytes according to their morphological features (e.g., their size, the morphology of their nucleus and cytoplasm, and the presence or absence of granules) or the degree of dye uptake and performs classification and counting of them. At ordinary laboratories, 100-200 leukocytes are usually counted for each sample and the percentage of the total leukocyte count occupied by each type of corpuscle is recorded as a measured value.

The differential counting method has several disadvantages. First, microscopic observation must be preceded by cumbersome procedures for preparing a specimen that involve such steps as smearing a blood sample on a glass slide, fixing the corpuscles and staining them. Secondly, it is a great burden for the technician to identify subtle differences between corpuscles by microscopic classification and counting Thirdly, it is difficult even for a skilled technician to yield consistent counts by the manual method since aside from the small number of leukocytes computed, the smeared sample often has an uneven distribution of blood corpuscles.

Various methods have been proposed for eliminating these disadvantages of the manual method of leukocyte classification by achieving automation and such automated techniques may be roughly divided into two types. The first method consists of recording the images of corpuscles with a video camera or some other suitable imaging device and classifying the leukocytes by means of image processing on a computer. The operating principle of this method is similar to that of the conventional visual counting method but primarily due to the existence of many corpuscles that defy classification by processing with a computer, this method has not yet become an ideal alternative to the manual method. Furthermore, this method is not economically feasible since it requires sophisticated equipment which is large and costly.

The other approach toward automatic classification and counting of leukocytes is based on a flow system. In this method, a blood sample having corpuscles suspended in a diluent is permitted to flow in such a way that the corpuscles will individually (one by one) pass through a narrowed detecting area and leukocyte classification is made by analyzing the signal generated by the detector. This second method of leukocyte counting which makes use of a flow system is further subdivided into two categories.

In a method of the first category, an electrolyte in which all red cells that were present have been destroyed with a lysing agent so that only leukocytes will be suspended is permitted to flow through an orifice and the change in electrical impedance that occurs at the orifice when each corpuscle passes through it is detected, with the magnitude of the detected signal being used as a basis for classification of leukocytes.

A method of the second category is characterized by the use of a flow cytometer that comprises a light source, a flow cell that permits the blood cells in a sample to ±low one by one through a constricted channel, a photometric unit that detects light issuing from each blood cell, and an analyzer for analyzing the detected signals. In this method, the corpuscles in the sample which are stained are illuminated under light and the fluorescence emitted from the irradiated corpuscles is detected, optionally together with scattered light, with leukocyte classification being made in accordance with the intensity of the detected signals.

Techniques that fall within the category of this flow cytometric method are described, for example, in Japanese Patent Publication No. 853/1984 and L. A. Kamentsky, Blood Cells, 6, 121–140 (1980). According to these techniques, a blood sample is stained with 10 volumes of an acridine orange solution, incubated for 1 minute, and irradiated under a light source such as an argon ion laser. The green fluorescence and red fluorescence that are emitted from the individual corpuscles are measured and classification and counting of leukocytes are subsequently made based on a two-dimensional plot of the fluorescence measurements.

Other examples of techniques that are classified as being within the flow cytometric approach are shown in Unexamined Published Japanese Patent Application No. 20820/1975; H. M. Shapiro et al. J. Histochem. Cytochem., 24, (1) 396–411, (1976); and idem, ibid, 225 (8) 976–989, (1977). According to these methods, a blood sample is stained with 4 volumes of a Dye Solution I, incubated for 3 minutes, further mixed with 20% formaldehyde in a volume equal to the blood, mixed for 5 minutes, and diluted with a diluting Dye Solution II to obtain a concentration 15–20 times as low as the initial value. The so prepared specimen is subjected to measurement with a flow cytometer.

The flow cytometer employed in these methods used either three mercury lamps each of which produces a separate wavelength of light or three lasers, so as to excite the three fluorescent stains in the dye solutions. The parameters measured are three kinds of fluorescence, forward scattered light, 90° scattered light and absorbed light. Based on these six parameters, two-dimensional plots are constructed in four stages and analyzed to make leukocyte classification and counting.

Japanese Patent Application No. 213715/1986 filed on Sep. 10, 1986 discloses a one-step staining process consisting of staining a blood sample with a dye solution comprised of a buffer solution, inorganic salts and fluorescent stains. But this method has the problem that unlysed erythrocytes may adversely affect measurement data to produce unreliable results.

In the first version of the method that uses a flow system for leukocyte classification and counting, the disruption of erythrocytes is a prerequisite but depending on a blood sample, it is impossible to effect complete lysis of erythrocytes and the accuracy of measurements may be impaired in such a case.

The examples of the flow cytometric approach that are described in Japanese Patent Publication No. 853/1984 and Blood Cells, 6, 121–140 (1980) are characterized by performing measurements before dye absorption by the cells reaches an equilibrium, or at the time when the difference between the intensities of fluorescence from individual leukocytes attains a maximum during the staining process. However, the time required for attaining an appropriate level of fluorescence intensity in a sample whose leukocyte count is at either one of two extremes will be different from the time for a normal sample and an appropriate staining time must be selected for each sample. As a further problem, this method relies solely on the differential intensities of fluorescences for leukocyte classification and does not necessarily ensure precise separation between different leukocyte types such as lymphocytes and monocytes.

The other examples of the cytometric approach that are described in Unexamined Published Japanese Patent Application No. 20820/1975, J. Histochem. Cytochem., 24 (1) 396–411 (1976) and supra, 25 (8) 976–989 (1977) have the disadvantage that they involve many steps of operation, take a prolonged staining time and require the use of reagents in a complex system. Furthermore, practice of these methods requires a very sophisticated and costly apparatus that includes three light sources and which is capable of measuring six parameters. In addition, analysis of such a large number of parameters is inevitably complicated and requires an analyzer of large capacity.

The method described in Japanese Patent Application No. 213715/1986 has the following problem. Erythrocytes in the blood sample emit only fluorescence of very low intensity, so if all that is needed is to measure the intensity of fluorescence, erythrocytes will not interfere with the counting of leukocytes even if coincidence of erythrocytes and leukocytes occurs (i.e., erythrocytes and leukocytes pass through the detecting portion simultaneously). However, if one wants to measure the scattered light, erythrocytes which produce scattered light having an intensity comparable to that of the scattered light emitted from leukocytes will interfere with the counting of leukocytes. In this case, one may measure fluorescence and scattered light simultaneously and regard as leukocytes only the corpuscles that emit fluorescence having an intensity greater than a certain level. However, if coincidence of leukocytes and erythrocytes occurs, the scattered light from erythrocytes is superposed on the scattered light from leukocytes, thereby making it difficult to accomplish accurate measurement of scattered light from the leukocytes.

In the invention described in Japanese Patent Application No. 213715/1986, a blood sample is diluted by, for example, 20 folds so that the probability of coincidence of erythrocytes and leukocytes is reduced but the potential interference by erythrocytes cannot be completely prevented. Therefor, if eosinophils and basophils are excluded by measurement of the intensity of fluorescence and if the intensities of right-angle scattered light from the remaining three types of leukocytes, i.e., lymphocytes, monocytes and neutrophils, are plotted, the populations of the three leukocyte types cannot be completely separated from one another as shown in FIG. 2b.

If the sample is further diluted so that the probability of coincidence of erythrocytes and leukocytes is reduced to such a level that the potential interference by erythrocytes can be completely disregarded, the populations of lymphocytes, monocytes and neutrophils can be completely separated from one another as shown in FIG. 2c, which is a plot of the intensities of right-angle scattered light from these three types of leukocytes. However, in order to ensure the desired precision of measurement, at least about 10,000 leukocytes must be counted. Therefore, the practical value of diluting the blood sample is limited by the prolonged time required for completion of measurement.

The aforementioned problems associated with the interference by erythrocytes can be solved if they are eliminated from the blood sample by a suitable technique such as lysing but this idea has not been put to practice in the present art because of the absence of any erythrocyte eliminating method such as lysing that matches the conditions of staining. There is no prior art technique that performs lysing of erythrocytes into five types by staining with fluorochromes. Also, there is no technique available that successfully lyses only erythrocytes within one minute and which yet does not deteriorate the right-angle scattered light (morphological information) from leukocytes.

Blood samples for leukocyte counting that are free from erythrocytes are commonly prepared by the following methods.
i) lysing of erythrocytes
 a) treatment with a surfactant;
 b) treatment with an ammonium salt (e.g. NH$_4$Cl);
 c) hypotonic treatment (at physiological pH)
ii) separation
 d) centrifugation;
 e) sedimentation;
 f) others.

The methods (a) to (e) are briefly described below.
(a) Treatment with a surfactant:
This method inhibits subsequent staining and in addition to lysing of erythrocytes, it causes morphological changes in leukocytes such as the loss of cytoplasm and membrane, swelling and shrinking, thereby making it difficult to achieve 3-part differentiation of leukocytes by signals of scattered light.

Furthermore, leukocytes in the sample treated with a surfactant will experience morphological changes with time.

(1) Treatment with an ammonium salt
This method inhibits subsequent staining. In addition, the ammonium salt does not have a great ability to lyse erythrocytes and a thick sample that is a 20-fold dilution of the whole blood is difficult to prepare by this method. Furthermore, it takes as many as 3–5 minutes to achieve complete lysis of erythrocytes by method (b).

(c) Hypotonic treatment

This method leaves leukocytes intact while lysing erythrocytes by making use of the fact that leukocytes are more resistant than erythrocytes in hypotonic solutions. However, at a physiological pH and under conditions that cause complete lysis of erythorocytes, part of the leukocytes will be destroyed.

(d) Centrifugation, (e) Sedimentation

Both methods have such disadvantages as cumbersome and lengthy procedures, and high incidence loss and fluctuations in each leukocyte's count and ratio.

The present invention has been accomplished in order to solve the aforementioned problems of the prior art techniques for leukocyte classification and counting and it provides a reagent and a method that enable accurate classification and counting of leukocytes by simple procedures.

In one aspect, the present invention provides a reagent system of the following composition for use in classifying leukocytes into five types by flow cytometry:

(1) a dye that specifically stains eosinophils, such as Neutral Red;
(2) a dye that specifically stains basophils, such as Astrazon Orange G or Auramine O (with the former being particularly advantageous);
(3) a buffer such as phosphate, citrate, borate, Tris [tris-(hydroxy-methyl)-aminomethane], Hepes, glycine, carbonate collidine, or taurine: and
(4) an osmolarity compensating agent (i.e., an alkaline metal salt including an alkali metal salt and an alkaline earth metal salt).

In order to achieve a better resolution of monocyte fractions, the following constituent (5) may be added:

(5) a dye that specifically stains monocytes and which is at least one member selected from the group consisting of $DiOC_1(3)$, $DiOC_2(3)$, $DiOC_3$, $DiOC_5(3)$, $DiOC_6(3)$, TA-2 and 2-[γ-(1'-ethyl-4',5'-benzothiazolylidene)propenyl]-1-ethyl,4,5-benzoxazolium iodide [DiOC (3) being particularly advantageous].

The dyes used as constituents (1), (2) and (5) respectively have the following chemical structural formulae:

Neutral Red (C.I. No. 50,040 or C.I. Basic Red 5)

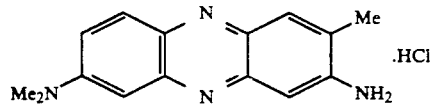

Astrazon Orange G (C.I. No. 48,035 or C.I. Basic Orange 21)

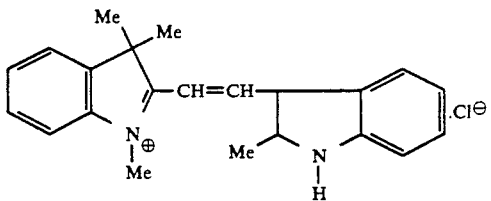

Auramine O (C.I. No. 41,000 or C.I. Basic Yellow 2)

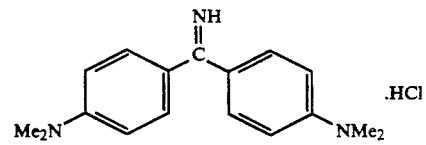

DiOCn(3) (1,1'-dialkyloxacarbocyanine); n = 1,2,3,5 or 6

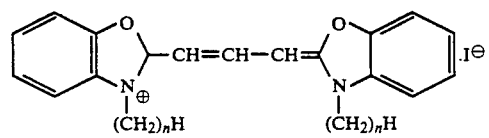

2-[γ-(1'-ethyl-4',5'-benzothiazolylidene)propenyl]-1-ethyl-4,5-benzoxazolium iodide

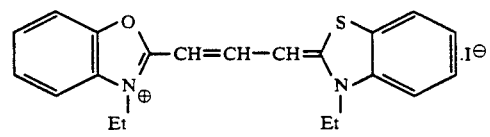

If the reagent system of the present invention is used, no complicated preliminary treatments are necessary and selective classification and counting of leukocytes can be accomplished with a flow cytometer by simply performing a one-step staining operation on the blood sample.

During the course of experimentation conducted on a trial-and-error basis that finally led to the accomplishment of the present invention, the present inventors found that there were 17 dyes with which leukocytes could be stained for classification into at least 4 different types based on two-dimensional plots of two of the parameters for measurement that consist of right-angle scattered light and several fluorescence emissions, with an argon ion laser that operates at 488 nm being employed as the sole light source. For the names, color index numbers and fluorescence characteristics of the individual dyes, see Table A below.

TABLE A

| Dye Group | Name | C.I. No. | Fluorescence Characteristics | |
|---|---|---|---|---|
| | | | Excitation maximum (nm) | Emission maximum (nm) |
| I. Xanthene dyes | Pyronine Y | 45.005 | 550 | 565 |
| | Rhodamine 3GO | 45.210 | 529 | 552 |
| | Fluorescein | 45.350 | 492 | 514 |
| II. Oxacarbocyanine dyes | DiOC1(3) | — | 480 | 497 |
| | DiOC2(3) | — | 481 | 498 |
| | DiOC3(3) | — | 483 | 500 |
| | DiOC5(3) | — | 485 | 499 |
| | DiOC6(3) | — | 483 | 499 |
| III. Acridine dyes | Acridine Orange | 46.005 | 493 | 528 |
| | Brilliant Phosphine | 46.035 | 459 | 505 |
| | Rhoduline Orange | 46.005 | 492 & 443 | 530 |

TABLE A-continued

| Dye Group | Name | C.I. No. | Fluorescence Characteristics | |
|---|---|---|---|---|
| | | | Excitation maximum (nm) | Emission maximum (nm) |
| | Euchrysin 3RX | 46.005 | 441 | 508 |
| | Flavophosphine R | 46.035 | 498 | 525 |
| | Coriphosphine O | 46.020 | 498 | 525 |
| IV. Azine dyes | Neutral Red | 50.040 | 518 | 625 |
| V. Diphenylmethane dyes | Auramine O | 41.000 | 463 | 515 |
| VI. Methine dyes | Astrazon Orange G | 48.035 | 470 | 529 |

*DiOC1(3): 1,1'-dimethyloxacarbocyanine
*DiOC2(3): 1,1'-diethyloxacarbocyanine
*DiOC3(3): 1,1'-di-(n-propyl)-oxacarbocyanine
*DiOC5(3): 1,1'-di-(n-pentyl)-oxacarbocyanine
*DiOC6(3): 1,1'-di-(n-hexyl)-oxacarbocyanine Leukocytes can be classified into five or more types if acridine dyes such as Acridine Orange and Rhoduline Orange are used.

FIG. 15 is a graph showing the resolution between eosinophils and neutrophils and that between basophils and neutrophils as a function of the concentration of Neutral Red;

FIG. 17 is a graph showing the resolution between eosinophils and neutrophils and that between basophils and neutrophils as a function of the pH of dye solution.

Figure 3:
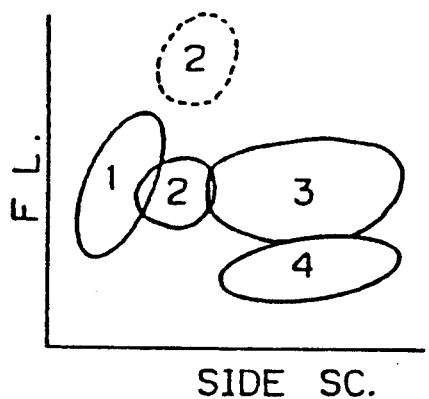
FIGS. 3 to 11 and 14 are two-dimensional plots of two signals as used to classify leukocytes.
Figure 4:
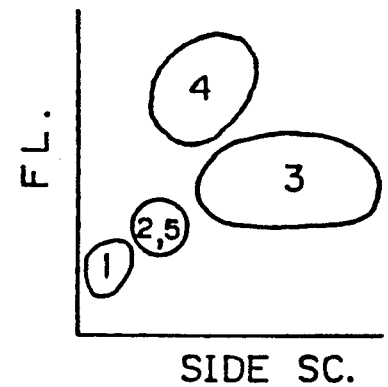
Figure 5:
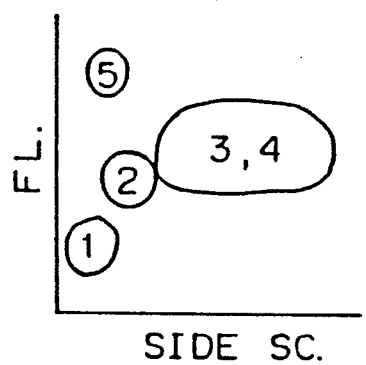

FIGS. 3 to 5 are two-dimensional plots of the intensities of right-angle scattered light and fluorescence as measured with a flow cytometer from leukocytes that were stained with one of the 17 dyes listed in Table A such that they were clearly distinguishable from erythrocytes and platelets. The numerals and symbols used in these figures have the following definitions: 1, lymphocytes; 2, monocytes; 3, neutrophils; 4, eosinophils; 5 basophils Side Sc., the relative intensity of right-angle scattered light; and FL., the relative intensity of fluorescence.

The separation pattern shown in FIG. 3 is typical of staining with Xanthene dyes, oxacarbocyanine dyes or acridine dyes. Similar patterns are obtained by constructing two-dimensional plots of the intensities of green and red fluorescence from leukocytes stained with acridine dyes.

The separation pattern shown in FIG. 4 is typical of staining with Neutral Red.

The separation pattern shown in FIG. 5 is typical of staining with Astrazon orange G or Auramine O.

Figure 6:
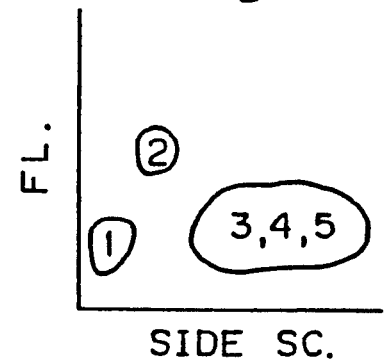

The present inventors also found that there were about 20 dyes with which luekocytes could be stained for classification into three types and the separation pattern that is typical of staining with these dyes is shown in FIG. 6.

Figure 7:
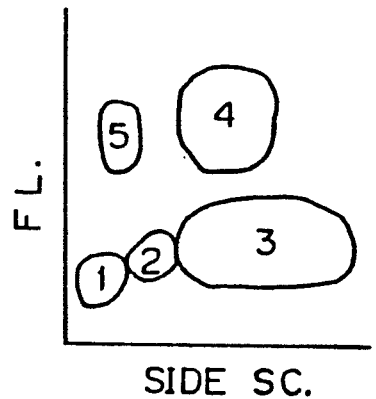
Figure 8:
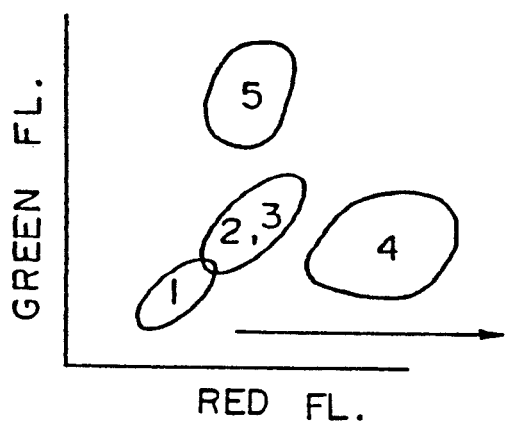
Figure 9:
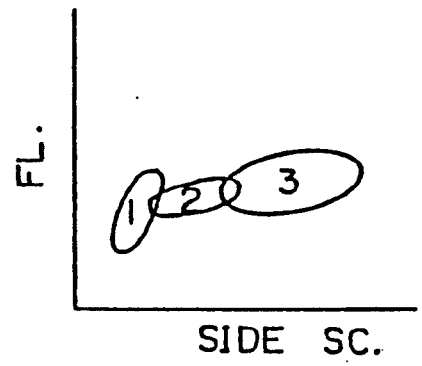

If one of the dyes that produce a separation pattern of the type shown in FIG. 4 is mixed with an appropriate amount of one of the dyes that produce a separation pattern of the type shown in FIG. 5, and if the fluorescence of each dye is received, a pattern of the type shown in FIG. 7 is produced by measurement of the intensities of fluorescence and right-angle scattered light. In this case, if Neutral Red of Azine dyes and Astrazon Orange G of Methine dyes are used, alternative two step analysis of three measurement parameters (i.e., right-angle scattered light, and red fluorescence and green fluorescence of appropriate wavelength) is possible. Eosinophils and basophils can be separated from other leukocyte types as shown in FIG. 8 (eosinophils 4 and basophils 5). The remaining components of leukocytes (i.e.,lymphocytes, monocytes and neutrophils) can be separated from one another by the intensities of fluorescence and right-angle scattered light as shown in FIG. 9.

Figure 10:
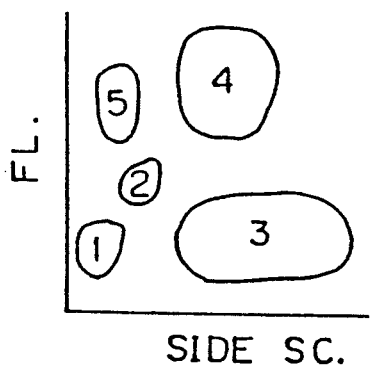
Figure 11:
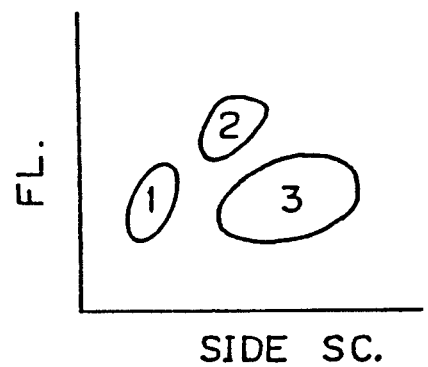

If a dye that produces a pattern of the type shown in FIG. 6 is added to dyes that produces the pattern of FIG. 7, a better resolution of lymphocytes, monocytes and neutrophils is achieved to produce a pattern of the type shown in FIG. 10 (in which the respective leukocyte populations are designated by 1, 2 and 3). In this case, too. A two-stage analysis can be effected by first employing green and red fluorescence (FIG. 8), then employing fluorescence and right-angle scattered light (FIG. 11). In the figures FL is fluorescent light that does not need to be limited to a specific wavelength, and it may be either green FL or red FL or fluorescent light having a wavelength longer than 520 nm.

Dye Characterization a. Neutral Red

This is a fluorochrome dye that selectively stains leukocytes. It stains eosinophils to a greater extent than other leukocytes. A two-dimensional plot of the intensities of right-angle scattered light and red fluorescence from leukocytes stained with Neutral Red is shown in FIG. 4.

Figure 12:
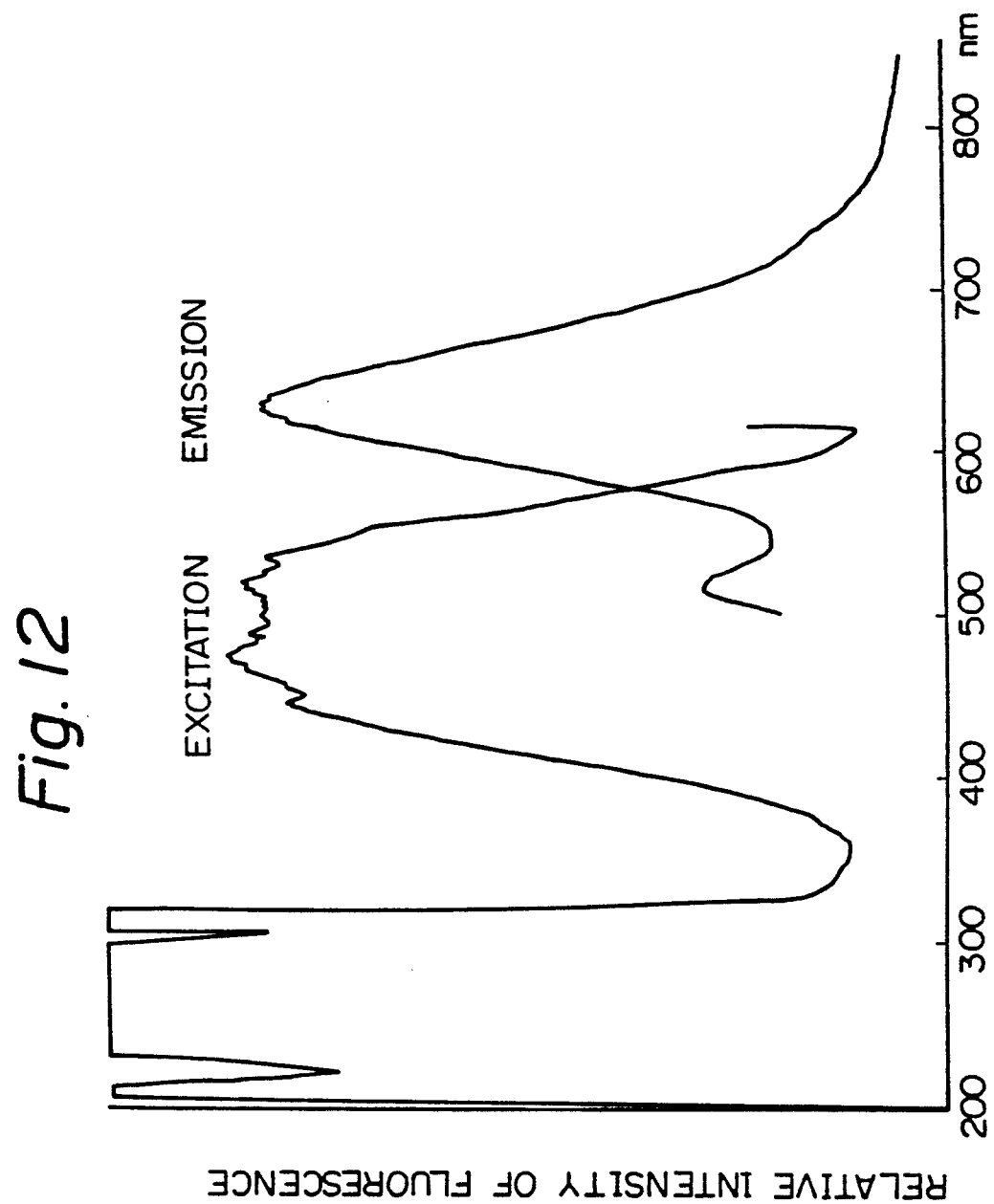
FIG. 12 is a graph showing the excitation and emission spectra of fluorescence of neutral Red.

FIG. 12 shows the excitation and emission spectra of fluorescence of Neutral Red Neutral Red produces a specific fluorescence of eosinophils in the band of 580–640 nm (orange to red).

A two-dimensional plot of the pattern shown in FIG. 4 is produced by using a dye solution having a pH of 5–11 and a dye concentration of 3–300 μg/ml. Even if the dye concentration is less than 3 μg/ml, a specific pattern of the distribution of eosinophils is produced but the other leukocytes are too noisy to be accurately measured. If one needs to obtain only the signal of eosinophils, the dye concentration may be at least about 0.1 μg/ml.

b. Astrazon Orange G

This is also a fluorochrome dye that selectively stains leukocytes. It stains basophils to a greater extent than other leukocytes. A two-dimensional plot of the intensities of right-angle scattered light and green fluorescence from leukocytes stained with Astrazon Orange G is shown in FIG. 5.

Figure 13:
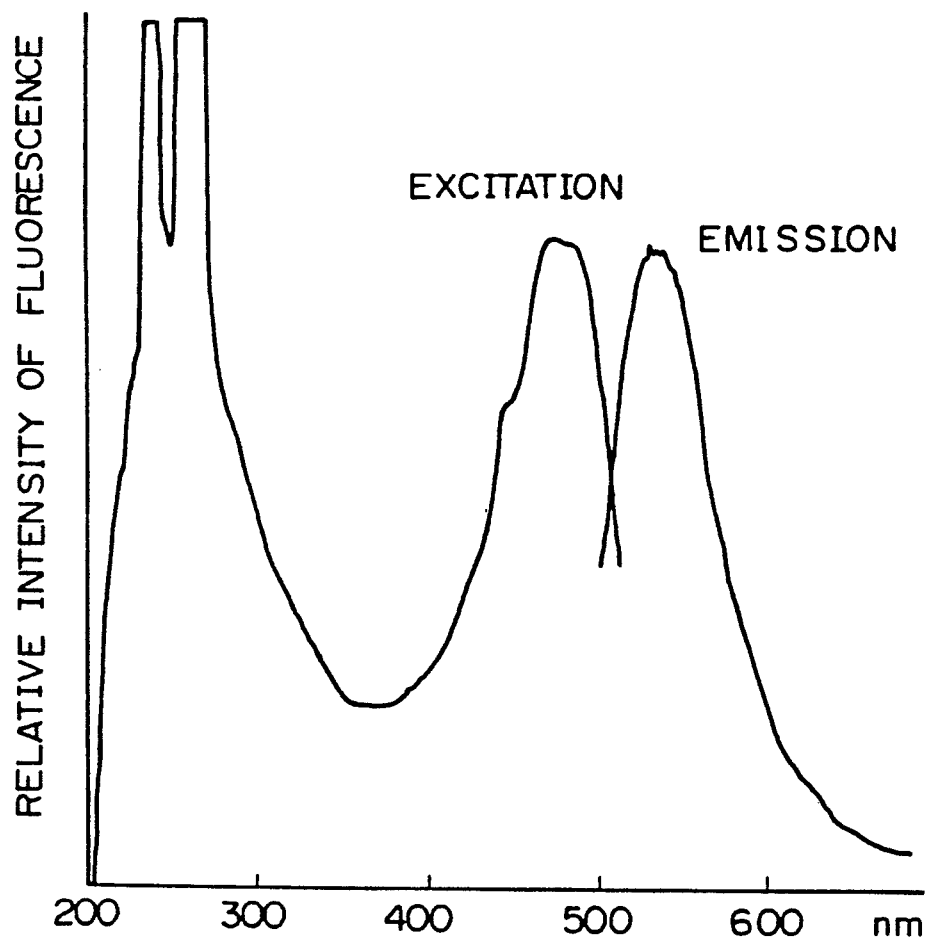
FIG. 13 is a graph showing the excitation and emission spectra of fluorescence of Astrazon Orange G.

FIG. 13 shows the excitation and emission spectra of fluorescence of Astrazon Orange G. Astrazon Orange G produces a specific fluorescence of basophils in the yellow-green band having a central wavelength of about 540 nm.

A two-dimensional plot of the pattern shown in FIG. 5 is produced by using a dye solution having a pH of 5–11 and a dye concentration of 1–300 μg/ml. A similar separation pattern is obtained with Auramine O.

c. Other dyes

Other fluorochromes that stain leukocytes can also be used. They stain monocytes to a greater extent than other leukocytes. They are capable of differentiating leukocytes into at least three types in terms of right-angle scattered light and fluorescence as shown in FIG. 6.

d. Combination of Neutral Red and Astrazon Orange G

Neutral Red produces a specific fluorescence of eosinophils while Astrazon Orange G specifically stains basophils, thereby producing a two-dimensional plot of the intensities of right-angle scattered light and yellow to red fluorescence as shown in FIG. 7. This plot is obtained by using a dye solution having a pH of 5–11, a Neutral Red concentration of 0.1–30 μg/ml, and an Astrazon Orange G concentration of 1–300 μg/ml.

e. Combination of Neutral Red, Astrazon Orange G and other dyes

By employing appropriate combinations of dyes of groups d. and c., leukocytes can be stained in such a way that a better resolution of monocytes (less contamination by lymphocytes and neutrophils) can be attained as compared with the case of using dyes of group d. alone. A two-dimensional plot of the intensities of right-angle scattered light and yellow to red fluorescence form leukocytes stained with combinations of Neutral Red, Astrazon Orange and other appropriate dyes is shown in FIG. 10.

Illustrative dyes that fall under category c. and which can be used to produce a separation pattern of the type shown in FIG. 10 include oxacarbocyanine dyes such as $DiOC_1(3)$, $DiOC_2(3)$, $DiOC_3(3)$, $DiOC_5(3)$ and $DiOC_6(3)$, TA-2 (a styryl dye produced by Nippon Kankoh-Shikiso Kenkyusho Co., Ltd., Okayama, Japan), and cyanine dyes such as 2-[γ-(1'-ethyl-4'-5'-benzothiazolylidene)-propenyl]-1-ethyl-4,5-benzoxazolium iodide.

Figure 14:
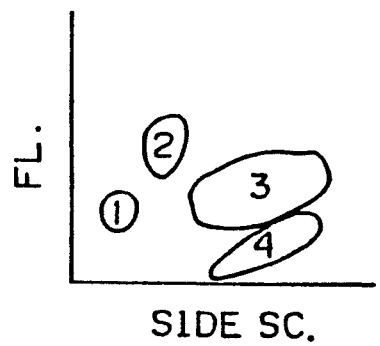

As shown in FIG. 14, oxacarbocyanine dyes used alone will allow leukocytes to be classified into 4 types, with eosinophils 4 stained to a smaller extent than neutrophils 3. If such dyes are mixed with Neutral Red which has a strong specificity for staining of eosinophils, a plot of the pattern shown in FIG. 10 is obtained, in which eosinophils 4 are distributed above neutrophils 3.

There are many other dyes that belong to group c. but because of several limiting factors such as dyeing conditions, degree of dye uptake and the wavelength of fluorescence emissions, those which are specifically mentioned above and analogs thereof are the sole examples that can be advantageously used in the present invention.

Other Components of the Dye Solution a. Buffer

The buffer is used to maintain the pH of the dye solution at an optimum level. It is important that the pH of the dye solution be maintained at an optimum level since a dye's adsorption mass and this specificity to cytoplasmic proteins vary with pH. Blood itself has a buffering action to maintain a pH near 7.4, so the buffer must be added in an amount sufficient to cancel this action and provide a desired pH.

For this purpose, buffers such as phosphate, citrate, borate, Tris, Hepes, glycine, carbonate, collidine and taurine are used in amounts ranging from 5 to 200 ppm.

b. Osmolarity compensating agent

The osmolarity compensating agent is used to prevent leukocytes from experiencing such defects as extreme deformation and lysis. For this purpose, alkaline metal salts are used in amounts of 60–380 mM so as to provide an osmolarity that is within the range of 40–250% of the physiological osmolarity of human blood (280 mOsm/kg).

In using the reagent system of the present invention, the following precautions must be taken:

(a) If two or more dyes are mixed together, dyeing conditions that permit the individual dyes to exhibit intended specificities must be located since optimum concentrations and pHs for achieving specific staining usually vary from dye to dye.

(b) The amount of each of the dyes to be added must be adjusted in such a way that a desired separation pattern is produced since different dyes have different intensities of fluorescence (fluorescence intensity is generally determined by multiplying the quantity of illuminating light, $I_o$, by the molecular extinction coefficient, $\epsilon$, quantum yield, $\phi$, dye concentration, c, and the compensation factor, $\alpha$, which is determined by the specific optics used), and (c) The wavelength of light to be received must be selected in such a way that a two-dimensional plot having a desired specificity can be obtained.

According to a second aspect of the present invention, it provides a method for classifying leukocytes by the following steps:

(a) lysing the erythrocytes in a fresh sample of anti-coagulated blood by adding it to a hypotonic first fluid composed of Neutral Red that selectively stains eosinophils, Astrazon Orange that selectively stains basophils, and a buffer for maintaining an acidic pH range;

(b) staining the leukocytes in the so-treated blood sample by adding to it a second fluid that is composed of a buffer for neutralizing the acid in the buffer in the first fluid and maintaining the pH of the resulting dye solution at a staining pH, and an osmolarity compensating agent for adjusting the osmolarity of the dye solution to a value at which the leukocytes remain unchanged in shape;

(c) permitting the stained sample to flow through a flow cytometer, differentiating leukocytes from all other corpuscles and ghosts by intensity of fluorescence, and measuring the signals of fluorescence and right-angle (rectangular) scattered light from leukocytes; and (d) identifying the type of each of the leukocytes based on said multiple signals emitted therefrom, counting the number of detected leukocytes according to their type, and calculating the proportions of individual leukocyte types.

Natural Red and Astrazon Orange G used in the method of the present invention have the following chemical formulae:

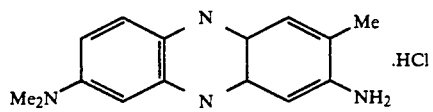

Neutral Red (C.I. No. 50,040 or C.I. Basic Red 5)

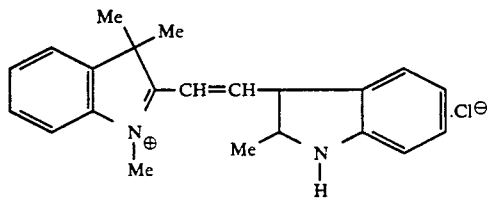

Astrazon Orange G (C.I. No. 48,035 or C.I. Basic Orange 21)

Of the multiple signals emitted from leukocytes in the method described above, the right-angle scattered light signal reflects the structural information of an individual white cell. The larger the nucleus of a white blood cell and the more granules that are present in it, the greater light reflection will occur in the cell to produce more intense right-angle scattered light. A lymphocyte contains very few or no granules, so the scattered light produced from the lymphocyte is the weakest of all leukocytes. On the other hand, a neutrophil contains many granules and has a large nucleus, so that it produces the intense scattered light.

Figure 2A:
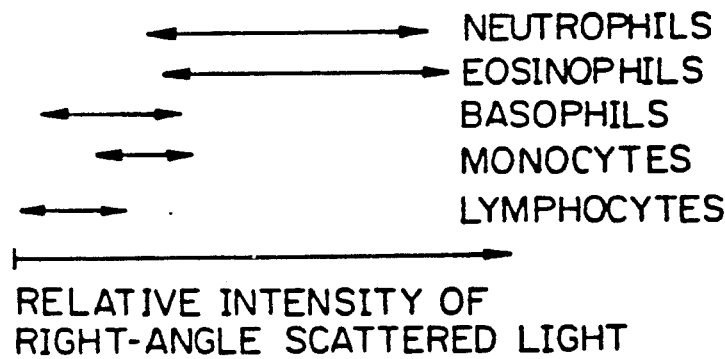
FIG. 2a is a graph showing the relative intensities of right-angle scattered light from five different types of leukocytes.
Figure 2B:
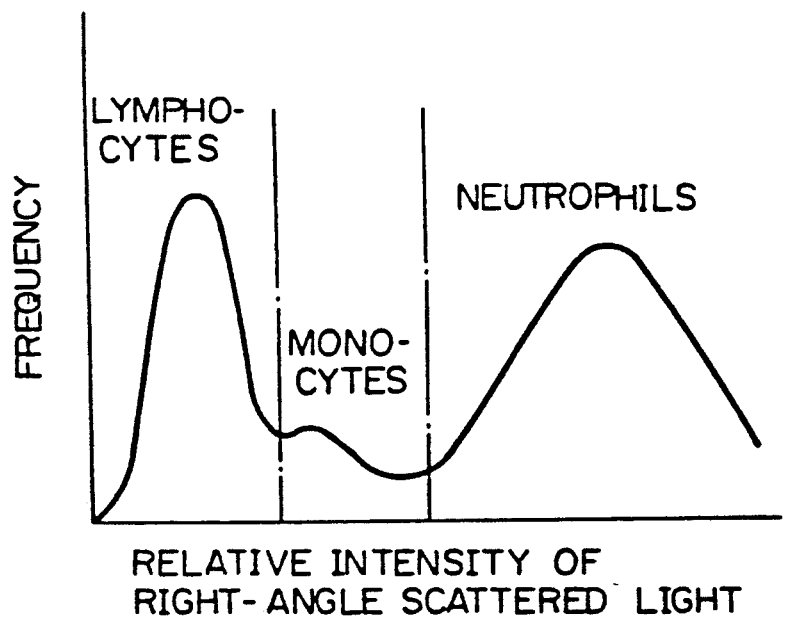
FIG. 2b is a frequency distribution curve for the intensities of right-angle scattered light from lymphocytes, monocytes and neutrophils as influenced by the coincidence of erythrocytes and leukocytes.

The intensity of scattered light which eosinophils produce is substantially equal to that of scattered light which neutrophils produce. Basophils produce scattered light the intensity of which is intermediate between the intensities of scattered light from lymphocytes and neutrophils. For these reasons, the relative intensities of right-angle scattered light from individual leukocyte types are plotted as shown in FIG. 2a.

The fluorescence signal reflects the cytochemical characters of leukocytes and depending on the interaction between stains and individual leukocyte types, signals of different intensities are produced from the leukocytes.

Therefore, leukocytes can be classified into five types by first performing selective staining of eosinophils and basophils so that the clusters of these two types of leukocytes can be separated from each other by the intensities of two fluorescences and subsequently differentiating the remaining leukocytes (i.e., lymphocytes, monocytes and neutrophils) by means of the intensity of right-angle scattered light.

As will be understood from the foregoing explanation, the method of the present invention has the advantage that no cumbersome operations involving a complicated preliminary treatment are required and that the leukocytes in blood alone can be classified and counted with a flow cytometer after a simple two-stage staining operation has been completed.

Figure 1:
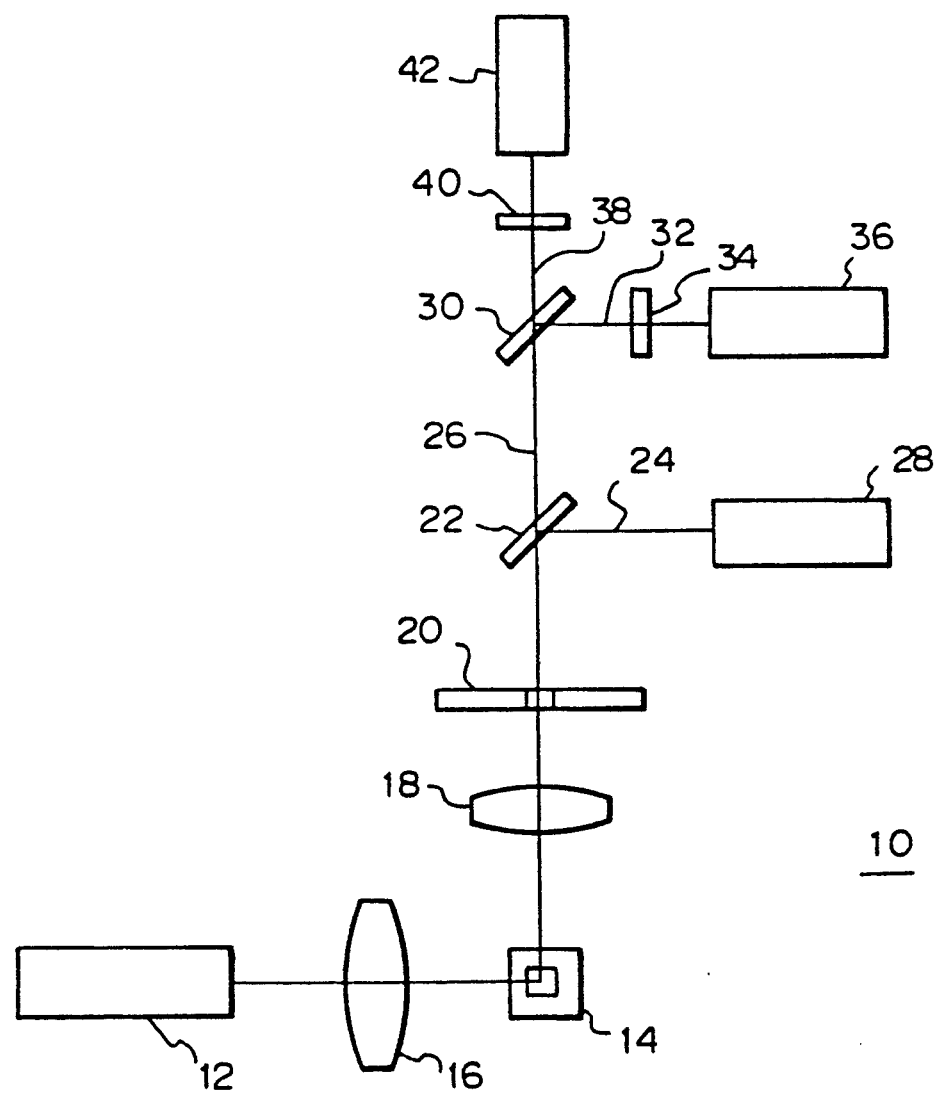
FIG. 1 is a schematic diagram of the optics of a flow cytometer that may be employed in implementing the method of the present invention.

A specific example of the optics of a flow cytometer employed in the present invention is hereunder described with reference to FIG. 1. The optics shown in FIG. I is used in a flow cytometer designed for measuring right-angle scattered light, red fluorescence and green fluorescence. The optics generally indicated by 10 uses an argon ion laser 12 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated by the laser light, they produce scattered light and fluorescence. The right-angle scattered light and the fluorescence are converged with a condenser lens 18 and pass through an aperture 20 to fall upon a dichroic mirror 22. The dichroic mirror 22 reflects the right-angle scattered light 24 and transmits the fluorescence 26. The right angle scattered light 24 reflected from the dichroic mirror 22 is detected in a photomultiplier tube 28. Of the two kinds of fluorescence 26 that passes through the dichroic mirror 22, red fluorescence 32 is reflected by a dichroic mirror 30 and green fluorescence 38 is transmitted through that mirror. The reflected red fluorescence 32 passes through a color filter 34 and is detected in a photomultiplier tube 36. The transmitted green fluorescence 38 passes through a color filter 40 and is detected in a photomultiplier tube 42.

In the method of the present invention, erythrocytes in a blood sample are disrupted by an acidic and hypotonic treatment such as to reduce the disturbance that occurs in the intensity distribution of right-angle scattered light on account of coincidence of red and white blood cells.

As already mentioned, if a hypotonic treatment is performed in the physiological pH range, not only the erythrocytes but also some leukocytes will be destroyed. On the other hand, if a hypotonic treatment is performed in an acidic pH range, for example, at a pH between 2.0 and 5.0, leukocytes will remain intact and only erythrocytes will be disrupted. In this case, no morphological changes such as the loss of cytoplasm and membrane swelling and shrinkage will occur in leukocytes.

The mechanism by which erythrocytes are selectively lysed is not clear but as erythrooytes are progressively lysed by hypotonic treatment, embrittlement of their membranes and acidic fixation of leukocytes will probably proceed under acidic pH conditions, with the result that only leukocytes which are more resistant than erythrocytes remain intact.

As a result of this hypotonic treatment under acidic conditions, most of the erythrocytes become "ghosts" and fragments. As a consequence, the intensity of right-angle scattered light signals from erythrocytes is reduced to no more than a half to a third of the intensity of right-angle scattered light signals from lymphocytes, and the coincidence of red and white blood cells can be disregarded for practical purposes.

Since not all of the erythrocytes are reduced to "fragments" by the hypotonic treatment under acidic conditions, it is difficult to discriminate erythrocytes from leukocytes solely on the basis of the intensity of scattered light signals. Therefore, as already mentioned, it is desirable to discriminate erythrocytes from leukocytes by the intensity of a fluorescence signal.

The functions of Astrazon Orange G and Neutral Red used as fluorochromes in the present invention are described below.

A sample of anti-coagulated blood is first mixed with the first fluid so that the erythrocytes in the blood are reduced to ghosts and fragments. Subsequently, the second fluid is added so as to stain the leukocytes and platelets in the blood.

It is speculated that the stains in the dye solution (i.e., first fluid) combine with the cellular constituents (granules, in particular) in the leukocytes by ionic adsorption. Astrazon Orange G would bind strongly to acidic substances such as heparin and histamine in basophilic granules and, as a consequence, the wavelength of fluorescence emitted from Astrazon Orange G shifts from 520–540 nm to 560–580 nm (this phenomenon is generally referred to as metachromasia). Astrazon Orange G also binds to the granules in the other leukocytes (i.e., eosinophils, lymphocytes, monocytes and neutrophils) but unlike in the case of its binding to basophils, no detectable metachromasia occurs. Astrazon Orange G binds weakly to the surfaces of nuclei and cells and emits fluorescence in the wavelength range of 520–540 nm.

Neutral Red also principally stains granules and emits fluorescence of 620 nm. This dye binds to eosinophilic granules to a greater extent than the granules in other leukocytes, thereby emitting a stronger fluorescence radiation than that emitted from any other leukocytes.

Figure 16:
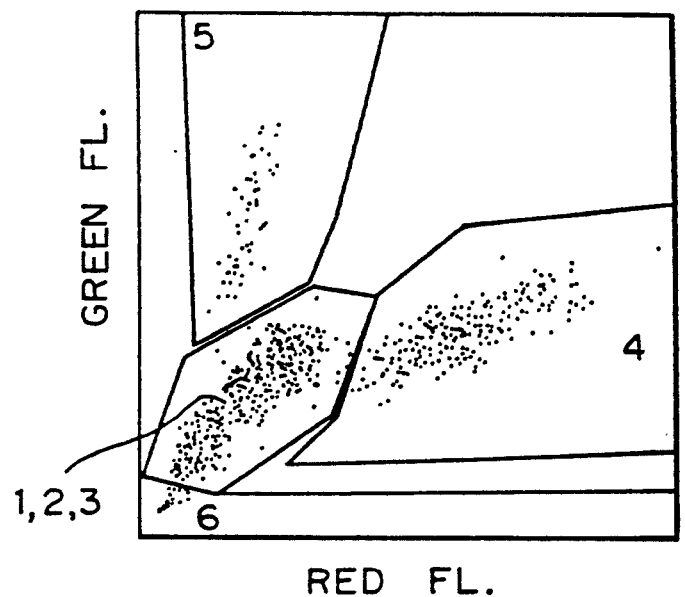
FIG. 16 is a two-dimensional plot of the intensities of red and green fluorescence as used to classify leukocytes.

A two-dimensional plot constructed from the measurement with a flow cytometer of a blood sample to which both the first and second fluids have been added is shown in FIG. 16, in which Red FL. signifies the relative intensity of red fluorescence and Green FL. denotes the relative intensity of green fluorescence. The numerals used in FIG. 16 have the following meanings 1, lymphocytes, 2, monocytes; 3, neutrophils; 4, eosinophils; 5, basophils; and 6, non-leukocytes, namely, platelets and erythrocytic ghosts and fragments (the same symbols and numerals used hereinafter have the same definitions).

Figure 2C:
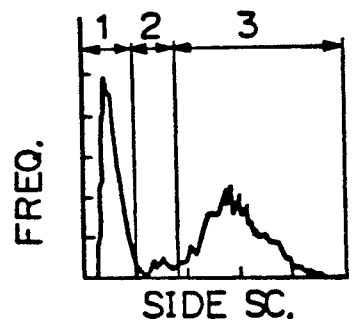
FIG. 2c is a frequency distribution curve for the intensities or right-angle scattered light from lymphocytes, monocytes and neutrophils in the absence of any coincidence of erythrocytes and leukocytes.

In FIG. 16, the leukocytes are clearly distinguished from platelets and erythrocytic ghosts and fragments denoted by 6 since the latter emit a lower intensity of green fluorescence. Eosinophils 4 and 5 are completely separated from others basophils in the two-dimensional plot of FIG. 16. However, the other leukocytes (i.e., lymphocytes 1, monocytes 2 and neutrophils 3) which do not emit any specific fluorescence cannot be separated from one another on the two-dimensional plot of the intensities of green and red fluorescences and can be classified as shown in FIG. 2c based on the intensities of right-angle scattered light.

The compositions, pHs and osmolarities of the first and second fluids used in the method of the present invention are described below in detail.

(1) Dye concentration
a. Concentration of Astrazon Orange G

Astrazon Orange G produces the best separation of basophils and neutrophils when its final concentration is 15 μg/ml with the staining pH being at 9.0. If the final concentration of Astrazon Orange G is less than 15 μg/ml, a lower resolution results because of the decrease in the intensity of green fluorescence from basophils. The same result also occurs if the final concentration of Astrazon Orange G is more than 15 ppm and this is because of the combined effect of the decrease in the intensity of green fluorescence from basophils and the increase in the intensity of green fluorescence from neutrophils. The concentration of Astrazon Orange G that provides an optimum resolution varies with pH. The adsorption mass of Astrazon Orange G decreases with decreasing pH.

b. Concentration of Neutral Red

A good resolution between eosinophils and neutrophils can be attained at the higher end of the concentration range of Neutral Red from 1 to 10 μg/ml. Eosinophils have better staining characteristics at lower pHs.

c. Interaction between Astrazon Orange G and Neutral Red

Neutral Red also stains the granules in basophils (i.e., the intensity of fluorescence it emits has no specificity to basophils), so it inhibits selective staining of basophils by Astrazon Orange G. It is therefore necessary to determine a concentration of Neutral Red that provides for good resolution between neutrophils and each of basophils and eosinophils.

FIG. 15 shows the profiles of resolution between eosinophils and neutrophils and between basophils neutrophils as a function of the concentration of Neutral Red with the concentration of Astrazon Orange G and pH fixed at 15 μg/ml respectively. In FIG. 15, the term "green fluorescence ratio of basophils/neutrophils" means the ratio of the intensity of green fluorescence from basophils to that from neutrophils, and the term "red fluorescence ratio of eosinophils/neutrophils" means the ratio of the intensity of red fluorescence from eosinophils to that from neutrophils (the same expressions used hereinafter have the same meanings). The higher the points in the figure, the better separation that can be achieved between neutrophils and basophils or eosinophils.

In FIG. 15, the separation between basophils and neutrophils coincides with that between eosinophils and neutrophils but in practice, there usually are fewer basophils in leukocytes than eosinophils, so in order to improve the resolution of basophils from neutrophils, it is desirable to set the concentration of Neutral Red at a comparatively low level, say 2 μg/ml.

If the volume ratio of the first to second fluid is set at 9:1 as in Example 7 to be described later in this specification, the concentrations of Astrazon Orange G and Neutral red in the first fluid may be adjusted to 16.5 μg/ml and 2.2 μg/ml, respectively, in order that their final concentrations will be at 15 ppm and 2 μg/ml, respectively.

(2) pH
a. Final pH to be attained as a result of mixing the first and second fluids FIG. 17 shows the profile of resolution between neutrophils and basophils or eosinophils as a function of pH, with the concentrations of Astrazon Orange G and Neutral Red being fixed at 15.0 ppm and 3.0 ppm, respectively. Obviously, the resolution of eosinophils from neutrophils decreases with increasing pH. On the other hand, the resolution of basophils from neutrophils increases with the increase in pH up to about 9.0–9.5 and decreases thereafter.

As pH increases, the rate of basophils staining increased (i.e., the time required for the intensity of fluorescence to reach a maximum) decreases, but once a maximum fluorescence intensity has been reached, the subsequent decrease in fluorescence intensity is rapid at high pH. The staining rate of eosinophils does not vary greatly with pH.

Therefore, with the resolution of neutrophils from each of eosinophils and basophils and the decrease in the intensity of fluorescence from basophils being taken into consideration, it is desirable to adjust the final pH to a value in the neighborhood of 8.6–8.7. In the present invention, the value of the final pH attained is referred to as the "staining pH".

b. pH of the first fluid

The pH of the first fluid influences the lysing efficiency of erythrocytes. Erythrocytes lyse rapidly at pHs of 5.0 and below, and the lower the pH, the faster the rate of lysis However, at pHs below 2.0, proteins such as hemoglobin begin to denature as the lysing of erythrocytes progresses, and the rate of protein denaturation increases as pH decreases. A denatured protein will clog at the time when the final "staining" pH has been attained. In consideration of these facts, it is desirable to adjust the pH of the first fluid to be at a value between 2.0 and 5.0.

(3) Buffer a. Buffer in the first fluid

The buffer in the first fluid is used to maintain the pH of the first fluid at a level suitable for lysing erythrocytes, and any buffer that has a pKa value of $3.5 \pm 1.5$ may be employed for this purpose. Illustrative examples include maleic acid, malonic acid, phthalic acid, diglycolic acid, saliyclic acid, fumaric acid, tartaric acid, citric acid and malic acid. In order to reduce the osmolarity of the first fluid, the concentration of the buffer is desirably held as low as possible. For the purposes of the present invention, the concentration of the buffer in the first fluid is preferably at 50 mM and below, more preferably at 5–30 mM.

b. Buffer in the second fluid

The buffer in the second fluid is used to neutralize the acid in the buffer in the first fluid and to maintain the pH of the resulting dye solution at the staining pH. Any buffer that has pKa value of 8.0–9.5 may be employed for this purpose. Illustrative examples include Tris, tricin, bicine, 2-amino-2-methyl-1,3-propanediol, taurine, boric acid and serine. These buffers are preferably used at concentrations of at least 10 mM in terms of the final concentration which is attained as a result of mixing of the first and second fluids. For the purposes of the present invention, the buffer in the second fluid advantageously has a final concentration of 30–100 mM.

(4) Osmolarity a. Osmolarity of the first fluid

The lower the osmolarity of the first fluid, the more rapid the lysing of erythrocytes. For the purposes of the present invention, the osmolarity of the first fluid is preferably adjusted to a value in the range of 0–100 mOsm/kg, more preferably in the range of 0–50 mOsm/kg.

b. Osmolarity of the second fluid

The osmolarity of the second fluid determines the final osmolarity which is to be attained as a result of mixing the first and second fluids. The final osmolarity influences the ability of leukocytes to retain their own shape and is preferably within the range of 150–600 mOsm/kg, more preferably in the range of 150–300 mOsm/kg.

The present invention is hereinafter described in greater detail with reference to the following Examples 1 to 7, which are given here for illustrative purposes only and are by no means intended to limit the present invention.

EXAMPLE 1

Concentration of Neutral Red and Astrazon Orange G

To a 10 mM borate buffer solution (pH, 9.0) containing 75 mM of NaCl, Astrazon Orange G and Neutral Red were added in the amounts shown in Table 1, so as to prepare dye solutions. Two milliliters each of these dye solutions were mixed with 80 μl of a fresh sample of EDTA anti-coagulated blood and the mixture was incubated for 1 minute. The so prepared specimens were permitted to flow through a flow cytometer having the optical arrangement of the composition shown in FIG. 1. The results of leukocyte classification based on the measurement of the intensities of green fluorescence, red fluorescence and right-angle scattered light are shown in Table 1.

TABLE 1

| Concentration of Neutral Red (μg/ml) | Concentration of Astrazon Orange G (μg/ml) | | | |
|---|---|---|---|---|
| | 3 | 10 | 30 | 100 |
| 0.3 | —*2) | 5*3) | 5*3) | —*2) |
| 1 | 3*5) | 5*1) | 5*3) | 3*5) |
| 3 | 4*4) | 5*3) | 4*4) | 4*4) |
| 10 | 4*4) | 4*4) | 4*4) | 4*4) |

*1) 5-part differentiation by red fluorescence*6) and right angle scattered light
*2) unclassifiable
*3) 5-part differentiation in which eosinophils and basophils were first separated from others by red fluorescence/green fluorescence,*7) followed by 3-part differential by right angle scattered light.
*4) 4-part differentiation by red fluorescence/right-angle scattered light;
*5) leukocytes were classified into 3 types by red fluorescence/green fluorescence; provided that;
*6) red fluorescence ≧ 580 nm: and
*7) green fluorescence = 520–580 nm.

EXAMPLE 2 pH

A dye solution having a pH of 8.0 was prepared by adding 10 μg/ml of Astrazon Orange G and 1 μg/ml of Neutral Red to a 10 mM borate buffer solution containing 75 mM of NaCl. Two additional dye solutions were prepared in the same manner as described above except that their pHs were adjusted to 9.0 and 10.0, respectively. Using these dye solutions, flow cytometry was conducted as in Example 1. With the dye solution having a pH of 10.0, 5-part differentiation of leukocytes could not be successfully achieved by measurement of the intensities of red fluorescence and right-angle scattered light. But the intended results could be attained by first differentiating basophils 5 from eosinophils 4 from others in terms of green fluorescence and red fluorescence and then distinguishing between the remaining three types of leukocytes based on green fluorescence and right-angle scattered light. With the dye solution having a pH of 9.0, 5-part differentiation of leukocytes could be accomplished based on red fluorescence and right-angle scattered light. With the dye solution having a pH of 8.0, 4-part differentiation was possible on the basis of the red fluorescence and right-angle scattered light.

EXAMPLE 3

Concentration of NaCl

Four dye solutions were prepared by adding 50, 75, 150 and 300 mM of NaCl to a 10 mM borate buffer solution (pH, 9.0) containing 10 μg/ml of Astrazon Orange G and 1 μg/ml of Neutral Red. Using these dye solutions, flow cytometry was conducted as in Example 1. No significant changes in separation pattern were observed within the tested range of NaCl concentrations and 5-part differentiation of leukocytes could successfully be achieved with each of the dye solutions.

EXAMPLE 4

Concentration of buffer

A dye solution was prepared by adding 75 mM NaCl, 10 μg/ml of Astrazon Orange G and 1 μg/ml of Neutral Red to a borate buffer solution (pH, 9.0) wherein the buffer was incorporated in an amount of 3 mM. Two additional dye solutions were prepared in the same manner as described above except that the buffer concentration was adjusted to 10 mM and 30 mM, respectively. Using these dye solutions, flow cytometry was conducted as in Example 1. No significant changes in separation pattern were observed within the tested range of buffer concentrations and 5-part differentiation of leukocytes could successfully be achieved with each of the dye solutions.

EXAMPLE 5

Wavelength of Fluorescence

Flow cytometry was conducted as in Example 1 using a dye solution that was composed of a 10 mM borate buffer solution (pH,9.0) containing 75 mM NaCl, 10 μg/ml of Astrazon Orange G and 1 μg/ml of Neutral Red. The analysis was based on the measurement of the intensities of right-angle scattered light and six fluorescence emissions not shorter in wavelength than 520 nm, 540 nm, 560 nm, 580 nm, 600 nm and 620 nm, respectively, that were collected with a photomultiplier tube 36 in the optics shown in FIG. 1. A total reflection mirror was used as a dichroic mirror 30, and a long-pass filter as a color filter 34.

As the wavelength of fluorescence collected was increased, the resolution between basophils and lymphocytes decreased whereas the resolution between eosinophils and neutrophils increased. The efficiency of 5-part differentiation of leukocytes was particularly high when fluorescence emissions having wavelengths not shorter than 560 nm and 580 mn were collected.

EXAMPLE 6

Wavelengths of Red and Green Fluorescence

Flow cytometry was conducted as in Example 5, with the wavelengths of red and green fluorescence collected being varied as shown in Table 2 below.

TABLE 2

|   | Green fluorescence (nm) | Red fluorescence (nm) |
|---|---|---|
| a. | 540–600 | ≧560 |
| b. | 540–600 | ≧580 |
| c. | 540–580 | ≧560 |
| d. | 540–580 | ≧580 |

TABLE 2-continued

|   | Green fluorescence (nm) | Red fluorescence (nm) |
|---|---|---|
| e. | 500–540 | ≧560 |

When fluorescence emissions having the wavelengths c. or e. were collected, basophils and eosinophils were selectively stained to permit good resolution from the other leukocytes.

The foregoing examples show that the reagent system of the present invention will produce good results when it is used under the following conditions.

| Astrazon Orange G: | 3–100 μg/ml |
|---|---|
| Neutral Red: | 0.3–10 μg/ml |
| pH: | 8.0–11.0 |
| Fluorescence wavelength | |
| Green Fl.: | 500–580 nm |
| Red Fl.: | ≧560 nm |

EXAMPLE 7

This is an example of the method of the present invention as it was carried out with the composition of the reagent system described above being adjusted to an optimum range.

| Reagents: | |
|---|---|
| 1) First fluid | |
| Astrazon Orange G (selective dye for basophils) | 16.5 ppm |
| Neutral Red (selective dye for eosinophils) | 2.2 ppm |
| Citric acid/sodium hydroxide (buffer) | 10 mM |
| pH, 3.0; osmolarity, 10 mOsm/kg | |
| 2) Second fluid | |
| Taurine/sodium hydroxide (buffer) | 500 mM |
| Sodium chloride (osmolarity compensating agent) | 300 mM |
| pH. 9.7–9.8; osmolarity, | 2,600 mOsm/kg |

Staining Procedure

Eighteen parts by volume of the first fluid was added to one part by volume of EDTA 2K anti-coagulated blood. After agitation, the mixture was incubated at 25° C. for 20 seconds. Thereafter, 2 parts by volume of the second fluid was added and, after agitation, the mixture was incubated at 25° C. for 40 seconds. The finally attained staining conditions were a pH of 8.7 and an osmolarity of 260 mOsm/kg.

Emission Characteristics of Fluorescence

The fluorescence emission intensity vs. wavelength characteristics of the individual leukocyte types as stained with the reagent system described above are shown in FIG. 18.

Selection of Filtration and Dichroic Mirrors

Figure 18:
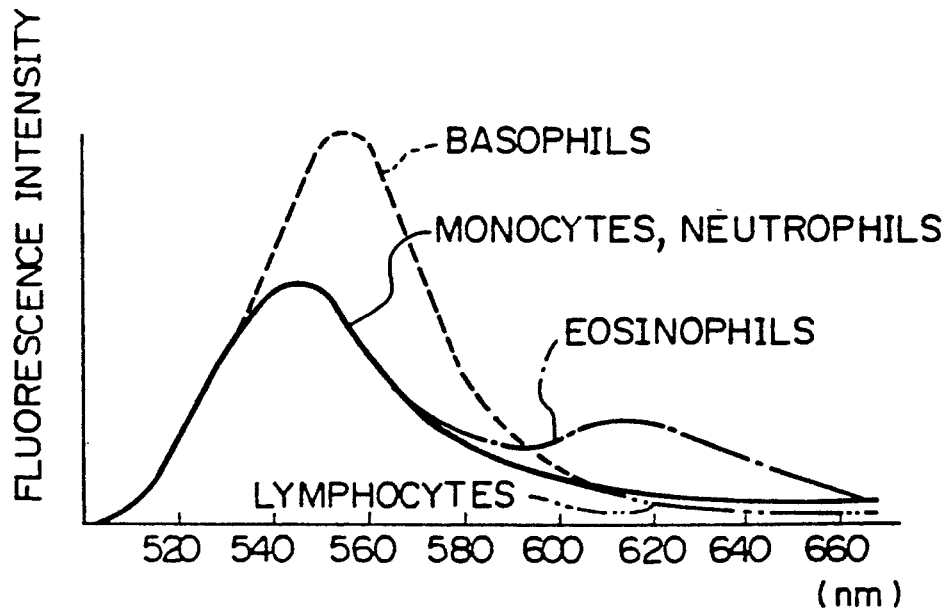
FIG. 18 is a graph showing the relation between the intensities of fluorescence of classified leukocytes and wave lengths.

Based on the emission characteristics shown in FIG. 18, the following filters and dichroic mirrors were selected as optimum devices:

| | |
|---|---|
| Dichroic mirror 22 | 530 nm (reflect blue light) |
| Dichroic mirror 30 | 600 nm (reflect red light) |
| Color filter 34 | 600 nm (long-pass filter transmitting wavelengths not shorter than 600 nm) |
| Color filter 40 | 540 nm (long-pass filter transmitting wavelengths not shorter than 540 nm) |

Results of Analysis

A two-dimensional plot of the intensities of red and green fluorescences as measured with a flow cytometer under the conditions described above is shown in FIG. 16. Population 6 (consisting of platelets, red cell ghosts and fragments) was successfully separated from leukocytes, and it was possible for both an eosinophil cluster 4 and a basophil cluster 5 to be separated from all other leukocytes with high resolution. The remaining leukocytes will also successfully be separated from one another with good resolution, as indicated in FIG. 2c which is a frequency distribution curve for lymphocytes 1, monocytes 2 and neutrophils 3. In FIG. 2c, Side Sc. signifies the relative intensity of right-angle scattered light and Freq stands for frequency.

In Examples 1 to 7, all measurements are initiated after the necessary procedures of staining have been completed (namely, after staining has reached an equilibrium). Therefore, the sample will not experience any time-dependent change during measurements, and an appropriate level of the intensity of staining or reaction can be attained within a certain period of time no matter how large or small the number of leukocytes in the sample is. This allows for consistent results in measurement and a fluorescence signal of an adequate intensity can be attained even if a light source of a comparatively low output is used. In Examples 1-7 described above, an argon ion laser of 10 mW was employed as a light source in the flow cytometer.

However, the light source in the flow cytometer used in the present invention is not limited to the afore-mentioned argon ion laser of low output and any of the other light sources can be employed, such as a mercury arc lamp, xenon arc lamp a He-Cd laser a He-Ne laser and a krypton ion laser, as well as an argon ion laser of high output. If these light sources are used, the conditions of staining, reaction and measurement may be selected as appropriate.

The reagent system and the method of the present invention as applied to classify and count leukocytes in blood by flow cytometry have the following advantages.

(1) A sample of measurement ban be prepared by simple preliminary treatments that consist of merely adding anti-coagulated blood to a dye solution.

(2) The sample can be prepared in approximately one minute and this provides a rapid access time for measurement.

(3) Since measurements are conducted after the necessary procedures of staining have been completed, the sample will not experience any time-dependent change during measurements and an appropriate intensity of staining or reaction can always be attained within a certain period of time irrespective of the nature of the sample (whether it is normal or contains an extremely large or small number of leukocytes). This eliminates the need to change the staining time from sample to sample.

(4) Since measurements are conducted after staining has been completed to provide a high staining intensity, a light source of low output may be employed. In addition, only one light source need to be used and two or three parameters appropriately selected from among two channels of fluorescence and one channel of right-angle scattered light may be measured. Because the number of parameters to be measured and analyzed in this few, the reagent system of the present invention can be used to accomplish flow cytometry of blood with a simple and inexpensive apparatus.

(5) The reagent system of the present invention has a very good ability to stain blood cells in a differential manner and therefore enable leukocytes to be classified with good resolution.

(6) The method of the present invention effects measurement not only of fluorescence but also of right-angle scattered light and this contributes to better classification of leukocytes including separation between lymphocytes and monocytes.

(7) In accordance with the method of the present invention, erythrocytes are selectively lysed by an isotonic treatment under acidic conditions. Since the coincidence of erythrocytes and leukocytes is eliminated by this treatment, a very efficient separation between lymphocytes, monocytes and neutrophils can be achieved by means of a right-angle scattered light signal.

(8) Leukocytes can be classified into five types with a very high resolution by first separating eosinophils from basophils on the basis of a fluorescence signal and then separating the remaining leukocytes (i.e. lymphocytes monocytes and neutrophils) based on right-angle scattered light.

(9) In the method of the present invention, separation of leukocytes from other corpuscles including their ghosts and fragments is achieved on the basis of fluorescence intensity, so correct measurements are ensured even if not all erythrocytes have been reduced to fragments According to the method of the present invention, accurate and reproducible measurements are ensured by counting no less than 10,000 leukocytes for each sample.

What is claimed is:

1. A method for classifying leukocytes by flow cytometry that comprises the following steps (a) to (d):
    (a) lysing the erythrocytes in a fresh sample of anticoagulated blood by adding it to a hypotonic first fluid composed of Neutral Red for selectively staining eosinophils, Astrazon Orange or Auramine O for selectively staining basophils, and a buffer for maintaining an acidic pH range;
    (b) staining the leukocytes in the so-treated blood sample by adding it to a second fluid that is composed of a buffer for maintaining the acid in the buffer in the first fluid and maintaining the pH of the resulting dye solution at a staining pH, and an osmolarity compensating agent for adjusting the osmolarity of the dye solution to a value at which the leukocytes remain unchanged in shape;
    (c) permitting the stained sample to flow through a flow cytometer, differentiating leukocytes from all other corpuscles and ghosts by intensity of fluorescence, and measuring the signals of one or two fluorescence emissions and right-angle scattered light from leukocytes; and
    (d) identifying the type of each of the leukocytes based on said measured signals, counting the number of detected leukocytes according to their type, and calculating the proportions of individual leukocyte types.

* * * * *

UNITED STATES PATENT AND TRADEMARK OFFICE
CERTIFICATE OF CORRECTION

PATENT NO. : 5,296,378
DATED : March 22, 1994
INVENTOR(S) : Sakata et al.

It is certified that error appears in the above-indentified patent and that said Letters Patent is hereby corrected as shown below:

Claim 1, column 20, line 51, change "it to" to --to it--.

Claim 1, column 20, line 52, change "maintaining" to --neutralizing--.

Signed and Sealed this

First Day of October, 1996

Attest:

BRUCE LEHMAN

*Attesting Officer*   *Commissioner of Patents and Trademarks*